United States Patent [19]

Waltonen et al.

[11] Patent Number: 4,674,482
[45] Date of Patent: Jun. 23, 1987

[54] PULSE ELECTRO-MAGNETIC FIELD THERAPY DEVICE WITH AUTO BIAS CIRCUIT

[75] Inventors: James Waltonen, Haines; Larry L. Bauer, Baker, both of Oreg.

[73] Assignee: IRT, Inc., LaGrande, Oreg.

[21] Appl. No.: 842,520

[22] Filed: Mar. 17, 1986

Related U.S. Application Data

[63] Continuation of Ser. No. 649,706, Sep. 12, 1984, abandoned.

[51] Int. Cl.⁴ .............................................. A61N 1/42
[52] U.S. Cl. ............................... 128/1.5; 128/419 F; 128/423 R
[58] Field of Search .................... 128/1.3–1.5, 128/419 F, 419 R, 423

[56] References Cited

U.S. PATENT DOCUMENTS 3,915,151 10/1975 Kraus .
4,105,017 8/1978 Ryaby et al. .
4,428,366 1/1984 Findl et al. .

FOREIGN PATENT DOCUMENTS 1150361 7/1985 Canada .............................. 128/1.5
2445151 8/1980 France .
2533131 4/1984 France .............................. 128/1.5

OTHER PUBLICATIONS

A. T. Barker, "The Design of a Clinical Electromagnetic Bone Stimulator," *Clinical Physical Physiology Measurement.*

Primary Examiner—Lee S. Cohen
Attorney, Agent, or Firm—Kolisch, Hartwell & Dickinson

[57] ABSTRACT

A method of treating animal tissue with a time-varying, magnetic field and a device for producing such a field wherein a substantially unipolar, rectangular electromagnetic treatment signal having pulses of a predetermined frequency and amplitude is generated. The signal is transmitted to a coil wherein it induces a magnetic flux. The magnetic flux so produced is applied to a treatment site to promote healing of tissue. A biasing circuit is provided in the device to prevent the occurrence of a reverse polarity pulse upon the fall of the magnetic flux induced by the fall of the generated pulse and to diminish high frequency ringing at the beginning of a treatment signal.

13 Claims, 8 Drawing Figures

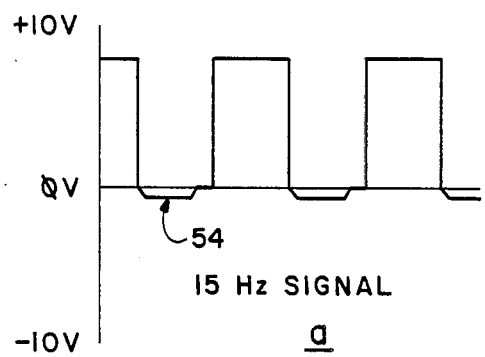
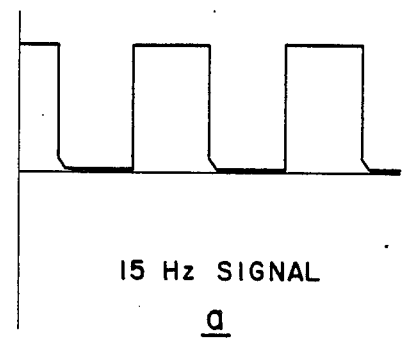
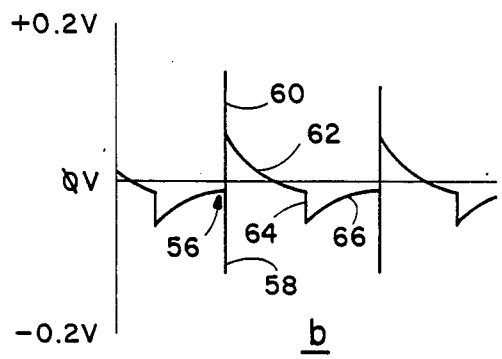
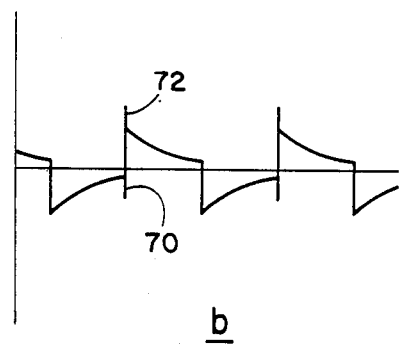
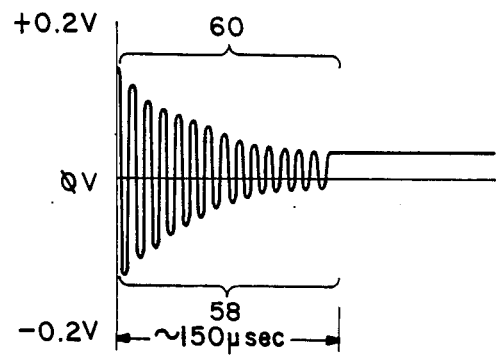
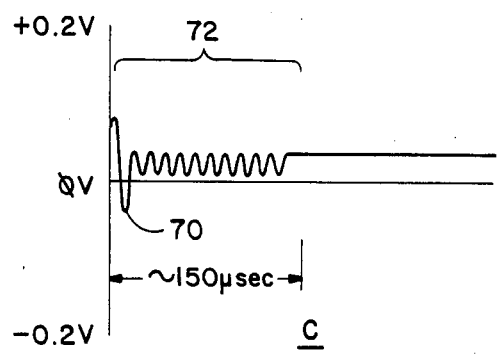
FIG. 3        FIG. 4

PULSE ELECTRO-MAGNETIC FIELD THERAPY DEVICE WITH AUTO BIAS CIRCUIT

This is a continuation of application Ser. No. 649,706 filed Sept. 12, 1984, now abandoned.

BACKGROUND AND SUMMARY OF THE INVENTION

The present invention pertains to a magnetic-field-producing therapy device for treating animal tissues with a time-varying magnetic field. Specifically, the therapy device of the instant invention generates a substantially only unipolar electro-magnetic pulse which assists a patient's bodily healing mechanism, thereby promoting faster healing of broken bones and enhancement of circulatory deficiencies.

The use of electrical energy to produce modifications in living tissue is well known. Electro-magnetic devices have been used to promote healing of broken bones. A. T. Barker, *The Design of a Clinical Electro-Magnetic Bone Stimulator, Clinical Physical Physiology Measurement,* February, 1981, Volume II, No. 1, Pages 9-16. Additionally, use of pulsed electro-magnetic fields (PEMF) to promote healing of bone tissue is described in U.S. Pat. No. 4,315,503 to Ryaby, et al. and in U.S. Pat No. 3,890,953 to Kraus, et al.

Use of electro-magnetic energy to arrest arthritic pain has been disclosed in U.S. Pat. No. 3,902,502 to Liss, et al.

A reading of the rather extensive literature in the field of electro-magnetic treatment teaches that there is little agreement amongst researchers in the field as to the most effective pulse wave form, frequency, and voltage level for treatment of tissue disorders. Without delving into the merits of one treatment method over the other, the present invention relates to an electro-magnetic-field-producing therapy device which generates a substantially rectangular, unipolar, electro-magnetic pulse of a predetermined frequency and amplitude and which includes a biasing means for preventing generation of a transient negative pulse when a positive, unipolar pulse collapses at the end of a duty cycle. The biasing means also substantially eliminates high frequency ringing at the beginning of a treatment pulse. A method of treating animal tissues with a time-varying, electro-magnetic field and apparatus for carrying out the method are taught. The method involves generating pulses in a frequency range of 1-100 hertz at an amplitude of 1-15 volts.

A basic premise of the teaching is that a negative pulse or spike which may form upon the collapse of a positive electro-magnetic field has a detrimental effect on the healing which is sought to be promoted by the application of the electro-magnetic pulse. Use of PEMF devices to promote vaso-constriction has not been successful due to the presence of high-frequency ringing at the beginning of a device duty cycle.

An object of the invention is to provide a method of treating animal tissue with a time-varying magnetic field, wherein the field is generated by a substantially rectangular, unipolar electro-magnetic pulse which is passed through a magnetic coil wherein the coil is biased to prevent the occurrence of a reverse polarity pulse upon the decay of the generated field.

Another object of the invention is to provide a device which will generate a magnetic field and which includes circuitry to prevent generation of a transient reverse polarity pulse upon the collapse of the generated field.

A further object of the invention is to provide a device which will be effective to form an electronic ice pack by acting as a vaso-constrictor.

In the preferred embodiment, a treatment pulse generator controls the frequency of magnetic pulses which are transmitted to a patient undergoing treatment. Circuitry is provided such that the initial frequency is ten times that of the ultimate treatment signal frequency, thereby allowing for substantially instantaneous adjustment of treatment signal frequency. This is particularly desirable when the device output is in very low frequency ranges, i.e. 0.1-20 hertz. A biasing circuit is provided in the device which induces an electrical current of the same polarity as the treatment signal through the treatment coils, thereby absorbing any reverse polarity spikes which may be generated simultaneously with collapse of the treatment signal generated field.

These and other objects and advantages of the instant invention and the method will become more fully apparent as the description which follows is read in conjunction with the drawings.

DESCRIPTION OF THE DRAWINGS

FIG. 3a-c is an illustration of wave forms produced and induced by the device without an operational biasing circuit.

FIG. 4a-c is an illustration of wave forms produced and induced by the device with a biasing circuit operating.

DETAILED DESCRIPTION OF THE DRAWINGS

Figure 1:
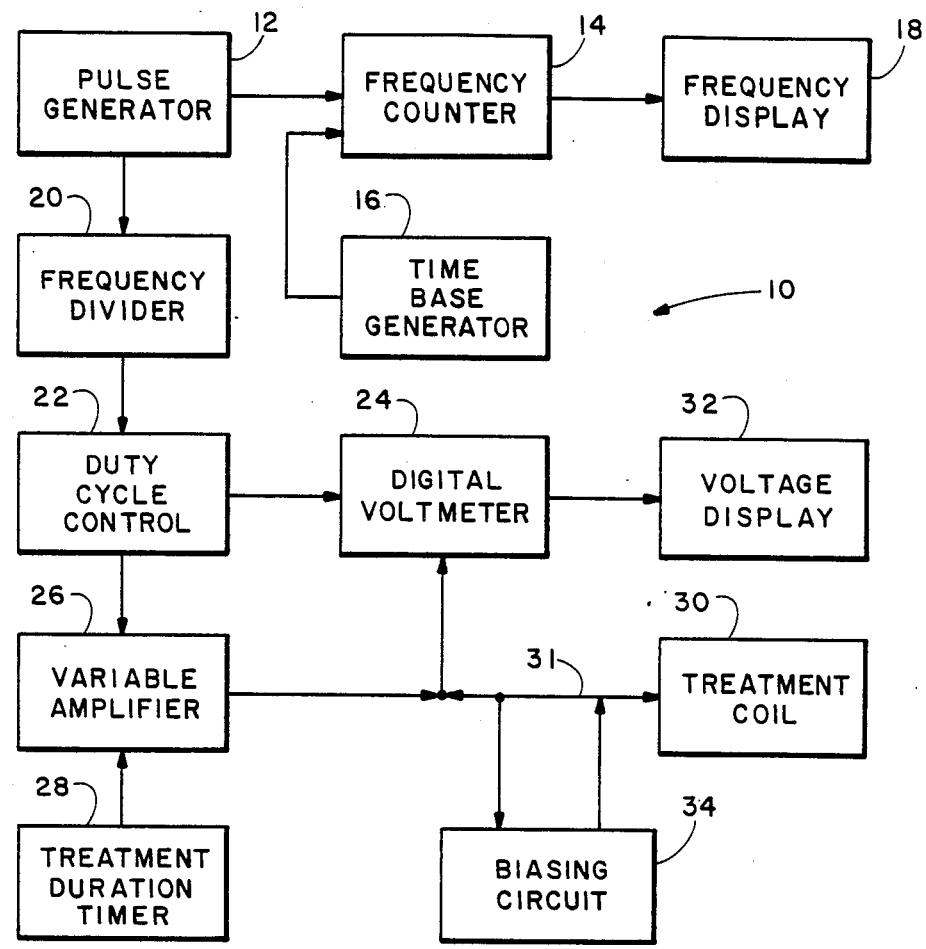
FIG. 1 is a block diagram of the magnetic-field-producing therapy device of the instant invention.

Turning first to FIG. 1, a block diagram of a magnetic-field-producing therapy device made according to this invention is shown generally at 10. Device 10 includes a pulse generator 12. A signal from generator 12 goes to frequency counter 14 where it is compared with a signal from a time base generator 16. Frequency counter 14 transmits a signal to a frequency display 18, which is a digital display in the preferred embodiment.

The frequency of the signal generated by pulse generator 12 is adjustable, and in the preferred embodiment, is generated at ten times the desired output frequency. It is therefore necessary to provide means for dividing the frequency produced by generator 12 to a usable, treatment frequency. This is accomplished by a frequency divider 20. The signal exits divider 20 and enters duty cycle control 22.

Two signals exit the duty cycle control. An update signal is transmitted to a digital volt meter 24. A treatment signal, of a desired treatment frequency, and of a known relation to the frequency of the signal generated by generator 12, is transmitted to an amplifier 26. Amplifier 26 is connected to a timer 28 which controls the duration of a treatment. Timer 28 may also be thought of as an off/on switch.

The treatment signal leaving amplifier 26 is transmitted to digital volt meter 24 and to a coil means, or, treatment coil, 30.

Digital volt meter 24 transmits a signal to voltage display 32. Thus frequency display 18 and voltage display 32 provide complete information as to the frequency and voltage (amplitude) of pulses being transmitted to the treatment coil.

The components 12 to 28 and 32 comprise what is referred to herein as pulse signal generating means.

A biasing circuit 34 provides a maintenance signal to treatment coil 30 at such times as the polarity of the signal in line 31 reverses from that of the treatment signal transmitted by amplifier 26.

Figure 2:
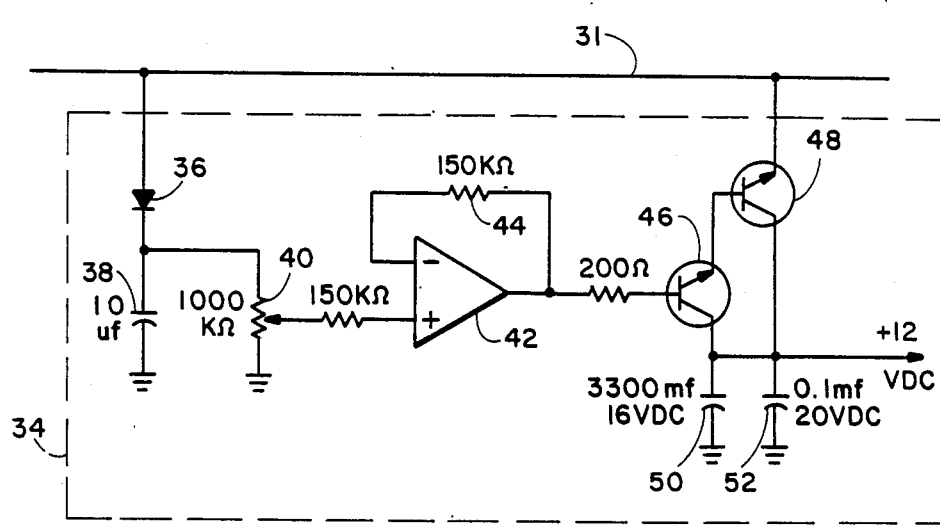
FIG. 2 is a schematic diagram of a biasing circuit incorporated into the therapy device.

Turning now to FIG. 2, biasing circuit 34 is shown in schematic form. As the treatment signal leaves amplifier 26, the signal is routed through line 31 and circuit 34. A diode 36 allows the treatment signal to enter the circuit when the signal is at a high level. The signal charges capacitor 38 and the remainder passes to variable potentiometer 40. The signal is then fed into op amp 42, which has a feedback loop 44 associated therewith. The signal next passes through Darlington-configured transistors 46 and 48, which together act as a series pass amplifier, providing a buffer between the op amp and treatment coil 30.

Capacitors 50 and 52 act as noise suppressors, preventing the biasing circuit from acting as an oscillator.

In use, pulse generator 12 initiates a treatment pulse cycle. The frequency of this cycle is adjustable and the frequency, divided by a known relation to the originally generated frequency, is ultimately displayed on display 18. The frequency of pulses generated by generator 12 is divided by a factor of 10, in the preferred embodiment, by frequency divider 20. Amplifier 26 may be varied to adjust the voltage which ultimately reaches the treatment coil and this value is displayed by voltage display 32. The signal which is produced by generator 12 is a substantially unipolar-rectangular wave in the frequency range of 1–1,000 hertz. Frequency divider 20 causes the output signal to range from 0.1 hertz to 100 hertz. Although the device is capable of producing a much higher frequency, it has been found that treatments conducted with pulses in the frequency range of 1–100 hertz are most beneficial to promoting healing of animal tissue defects sought to be treated. The device may be used as an electronic ice pack for vaso-constriction with frequency settings of 0.1 to 5 hertz.

As previously stated, the device of the instant invention is based on the premise that a unipolar electro-magnetic pulse is the most effective therapeutic wave form. To this end, the device generates a treatment signal which consists solely of positive portions of the rectangular signal. This is referred to herein as a unipolar pulse. Duty cycle control 22 causes the device to have a 50% duty cycle, thereby resulting in a substantially square, unipolar pulsed treatment signal. Other duty cycles may of course be used.

The amplifier has the capability of delivering high voltage at up to 15 amps, however, the output is generally in the range of 0.1–15 volts, with the most effective voltages being in the range of 5.75–12.5 volts. Such a voltage range results in a magnetic flux level of 4–22 gauss at the coil.

FIG. 3a represents a 15 hertz signal measured in line 31. As each unipolar pulse reaches the treatment coil, an electro-magnetic field is produced. As the pulse terminates, the electro-magnetic field collapses. This normally results in a negative or reverse polarity spike as is illustrated at 54. FIG. 3b represents the wave form as induced in a sensing coil by the magnetic field generated in coil 30 by the pulsed treatment signal shown in FIG. 3a. Referring still to FIG. 3b, as a steady state is reached, at 56, the wave approaches the ground or reference line. Upon initiation of a treatment pulse, the induced pulse initially is formed as a rather large negative impulse 58 which is immediately followed by a positive spike 60. This ringing oscillates for approximately 150 microseconds as depicted in FIG. 3c. As the ringing subsides, the induced voltage drops off as depicted by the curve at 62. When the treatment signal ceases, the induced voltage instantly drops, as shown at 64. The induced voltage gradually returns to a near-steady state, as shown at 66, prior to the next treatment pulse being generated.

The inclusion of the biasing circuit results in the signal form in line 31 shown in FIG. 4a. A maintenance signal of the same polarity as the treatment signal is transmitted to treatment coil 30 when a reverse polarity signal is present in line 31, as the result of the collapse of the field about coil 30. Biasing circuit 34 provides a small voltage, on the order of 0.2 volts to coil 30 when the generator means is in a non-duty cycle. As the duty cycle ends, the field about coil 30 collapses, resulting in a reverse polarity signal in line 31. The presence of such a signal in line 31 "triggers" circuit 34 to transmit a signal component of the same polarity as the treatment signal into line 34, thereby offsetting the reverse polarity signal present in the line. The maintenance signal slightly elevates the wave form above the reference line, as depicted in FIG. 4a at 68, as opposed to negative spike 54 depicted in FIG. 3a.

The wave form depicted in FIG. 4b which is induced in a sensing coil by coil 30 when the biasing circuit is in operation, has spikes, as shown at 70, 72, but does not exhibit the extreme spikes, such as 58 and 60 depicted in FIG. 3b, as when the biasing circuit is not operating. Although a high frequency ring still occurs at the peak, the ring has a much smaller amplitude, as depicted in FIG. 4c, than does the ring generated by a non-biased signal, and more important, has only one reverse polarity spike, as shown at 70. The duration of the ring is proportional to the treatment frequency.

The strength of the maintenance signal is determined by the biasing circuit, and specifically by the setting on variable potentiometer 40. Potentiometer 40 is calibrated in terms of device output, from 0 to 100%. If, for instance, potentiometer 40 is adjusted to a value of 20% of device output, a maintenance signal 20% the strength of the treatment signal will be fed to coil 30 when the treatment signal terminates and the magnetic field collapses. A maintenance signal 20% the value of the treatment signal has been found to eliminate any negative value, or negative spike, generated by the collapse of magnetic field about treatment and coil 30.

A specific use of the device and method of the invention is exemplified by a treatment which may be applied to an animal limb which has, for instance, suffered a bruise. The device may be used to form an electronic ice pack. As previously mentioned, known PEMF devices have not been able to promote vaso-constriction due to high frequency wave forms which occur during the ringing at the beginning of the treatment pulse. A specific coil, formed of 329 turns of 22 gauge wire, may be applied to a treatment site and a voltage of 12.5 volts applied. With a frequency setting of 3 hertz, the coil will produce 22 gauss at the treatment site. This technique has been found to produce sufficient vaso-constriction to reduce the severity of bruising. The same coil and voltage settings, when used with a frequency of 15 hertz would be effective to treat soft collagen tissue damage. Various combinations of wire size, turns and voltages may be utilized, thereby producing magnetic flux of 0-60 gauss at coil means 30.

While a preferred embodiment of the invention has been described, it is appreciate of the variations and modifications may be made without departing from the spirit of the invention.

It is claimed and desired to secure by Letters Patent:

1. A magnetic-field-producing therapy device for treating animal tissues with a uni-directional, time-varying magnetic field comprising pulse signal generating means for generating a treatment signal characterized as having unipolar, rectangular electro-magnetic pulses of a known polarity at a predetermined frequency and of a predetermined amplitude relative to a reference level, biasing means operatively joined to said generating means, for producing, when the treatment signal is of a reverse polarity, a maintenance signal component completely offsetting the reverse polarity portion of said treatment signal, said biasing means including reverse polarity sensor means for sensing a reverse polarity portion of a treatment signal and maintenance signal generating means for generating a maintenance signal offsetting the reverse polarity portion of said treatment signal, and coil means operatively joined to said generating means for producing a concentrated magnetic flux from said treatment signal for use in applying the flux so produced to tissue undergoing therapy at a treatment site.

2. The therapy device of claim 1 wherein said treatment signal has a fifty percent duty cycle.

3. The therapy device of claim 1 wherein said generating means includes amplitude adjustment means for adjusting the predetermined amplitudes of the unipolar pulses, wherein said amplitude adjustment means is operable to vary the predetermined amplitude between 0.1-15 volts.

4. The therapy device of claim 3 wherein said coil means and generating means are cooperatively constructed such that said coil means produces a magnetic flux of 0 to 60 gauss.

5. The therapy device of claim 3 wherein said generating means further includes an adjustable pulse generator means for generating an output signal having pulses with a controllably variable known frequency, frequency readout means operatively joined to said pulse genertor means for displaying a frequency value having a known relation to the known frequency, and frequency divider means operatively interposed said pulse generator means and said amplitude adjustment means for producing, in response to said output signal, a lower frequency signal having pulses with a frequency equal to the known frequency multiplied by the previously-mentioned known relation.

6. The therapy device of claim 5 wherein said pulse generator means is adjustable to vary the predetermined frequency of the unipolar pulses between 0.1-100 hertz.

7. The therapy device of claim 1, wherein said maintenance generating means includes maintenance signal amplitude determination means for determining the amplitude of said maintenance signal as a function of said predetermined amplitude of said treatment signal.

8. A magnetic-field-producing therapy device for treating animal tissues with a uni-directional, time-varying magnetic field comprising pulse signal generating means for generating a treatment signal characterized as having unipolar, rectangular electro-magnetic pulses of a known polarity at a predetermined frequency and of a predetermined amplitude relative to a reference level, biasing means operatively joined to said generating means, for producing, when the treatment signal is of a reverse polarity, a maintenance signal component exactly offsetting the reverse polarity portion of said treatment signal to maintain said signal on one side only of said reference level, said biasing means including reverse polarity sensor means for sensing a reverse polarity portion of a treatment signal and maintenance signal generating means for generating said maintenance signal, said maintenance signal generating means including maintenance signal amplitude determination means for determining the amplitude of said maintenance signal as a function of said predetermined amplitude of said treatment signal, and coil means operably joined to said generating means for producing a concentrated magnetic flux from said treatment signal for use in applying the flux so produced to tissue undergoing therapy at a treatment site.

9. The therapy device of claim 8 which includes amplitude adjustment means operable to vary the predetermined amplitude between 0.1-15 volts, and wherein said pulse generating means generates an output signal having pulses with a controllably variable known frequency, and which further includes frequency divider means operatively interposed said pulse generating means and said amplitude adjustment means for producing, in response to said output signal, a signal having a predetermined frequency.

10. A method of treating animal tissue with a time-varying, pulses electro-magnetic field comprising generating a treatment signal characterized as having unipolar, rectangular electro-magnetic pulses of a predetermined frequency, producing a time-varying magnetic flux by energizing a coil with the treatment signal, generating, as a function of the treatment signal, a maintenance signal which, as a treatment signal pulse ceases, is transmitted to the coil to completely offset a reverse polarity pulse, and applying the magnetic flux to a treatment site.

11. The method of claim 10 wherein the generated signals have a frequency in the range of 0.1 to 100 hertz.

12. The method of claim 10 wherein the generated pulses have amplitudes in the range of 0.1 to 15 volts.

13. The method of claim 10 wherein the generated pulses generally have a duty cycle of fifty percent.

* * * * *